US00PP08187P

United States Patent [19]

Bailey

[11] Patent Number: Plant 8,187

[45] Date of Patent: Mar. 30, 1993

[54] APPLE TREE: DULCET CULTIVAR

[76] Inventor: L. James Bailey, 3900 Mylius Rd., Wenatchee, Wash. 98801

[21] Appl. No.: 697,881

[22] Filed: May 9, 1991

[51] Int. Cl.[5] ..... A01H 5/00

[52] U.S. Cl. ..... Plt./34.1

[58] Field of Search ..... Plt. 34, 34.1

*Primary Examiner*—James R. Feyrer

*Attorney, Agent, or Firm*—Christensen, O'Connor, Johnson & Kindness

[57] ABSTRACT

A new variety of apple tree of unknown parentage, exhibiting a distinctive deep red fruit coloration with prominent buff colored lenticels, a stubby stem, and large, flattened flowers.

5 Drawing Sheets

BACKGROUND OF THE INVENTION

The subject plant is a new and distinct variety of apple tree that was discovered as a chance seedling of unknown parentage in the orchard of L. James Bailey in Wenatchee, Wash. This new variety has been fruited through three successive generations, by budding and grafting in the discoverer's orchard and in the Van Well Nursery orchard at Wenatchee, Wash. The orchard where the new variety was found is a Red Delicious orchard with McIntosh pollenizers. The new apple resembles McIntosh more than it does Red Delicious; however, it can be readily distinguished from Red Delicious and McIntosh. The characteristics of this variety have remained the same through the three generations. The varietal name "Dulcet Cultivar" is proposed for the subject apple trees.

SUMMARY OF THE VARIETY

This new variety of apple tree is distinguished from other known varieties by its deep red colored fruit which have prominent tan or buff colored lenticels (dots). The deep red ground color, as identified using Ridgeway's Color Standards and Nomenclature, is bordeaux (Plate XII). The lenticels on the apple are characteristically colored Warm Buff (Plate XV in Ridgeway). The mature apple of this new variety also has a distinctive buff to green colored stem cavity. The apple is further characterized by a stubby (short and thick) stem. These distinctive characteristics are all shown in FIG. 1.

The large white blossoms of this new variety are also considered distinctive. As shown in FIG. 2, the large blossoms have a relatively flattened corolla, as compared to the more cup-shaped flowers of other apple tree varieties.

BOTANICAL DESCRIPTION OF "DULCET"

The subject apple trees are described in detail below.

TREE

Figure 3:
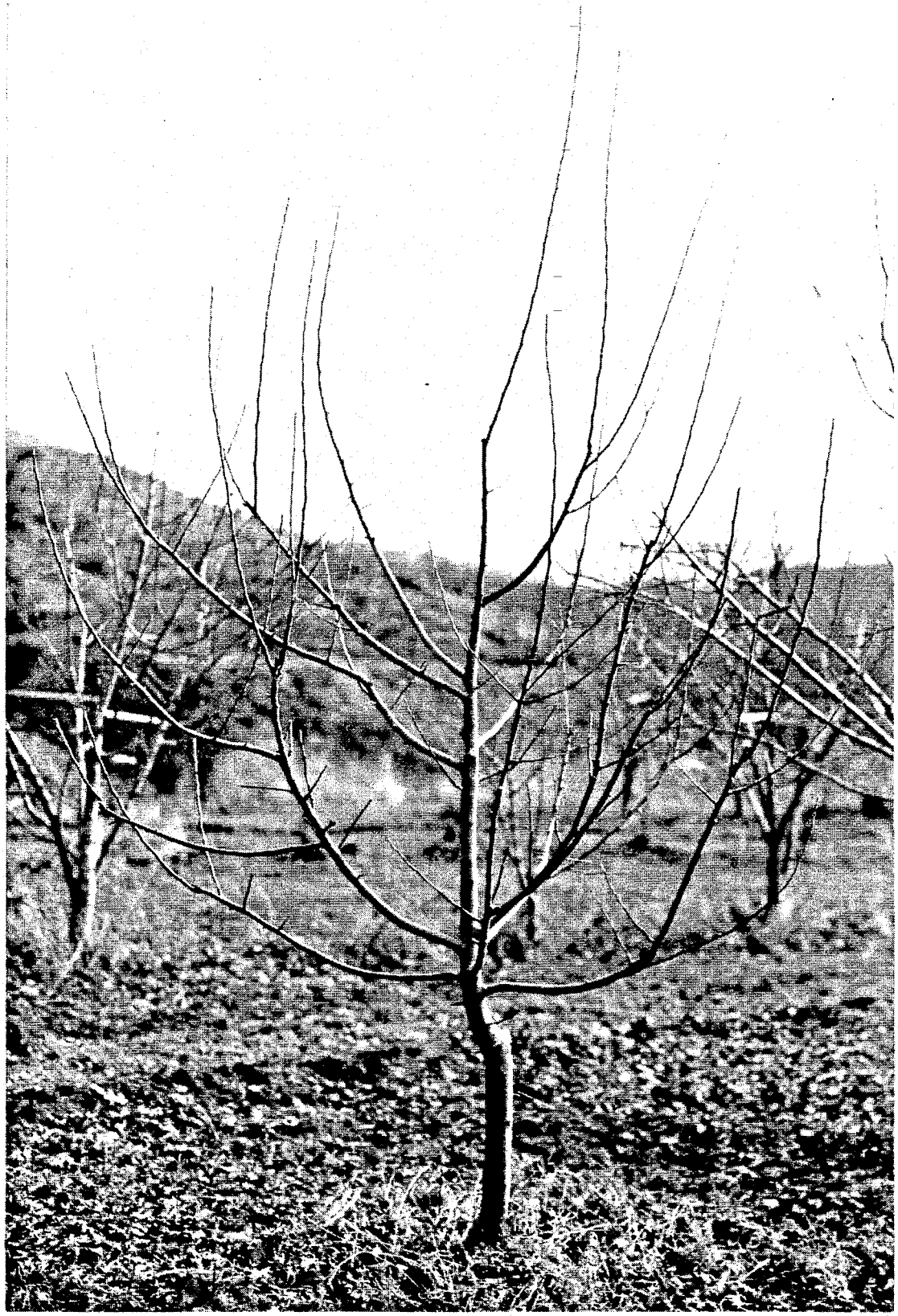
FIG. 3 illustrates a specimen of the claimed tree in dormancy, attained by budding onto a Malling 7*a* rootstock, which is being trained to a central leader, showing growth and branching habit of a specimen four years after bud placement.

Growth form: FIG. 3 shows a representative four-year-old tree of this new variety, here grafted on a Malling 7*a* rootstock and central leader trained. The subject trees are vigorous, of medium height with a spreading, open growth form. The ultimate tree width and height at maturity will be similar to the width and height of a Red Rome tree on any given rootstock. The average terminal growth on the fifth leaf "Dulcet" apple tree grown in Wenatchee, Wash. was 14 inches in length. This compares to an average length of terminal growth of 10 inches of a Rome tree in the same orchard. The trunk is medium (neither stocky nor slender), with smooth bark. The branches are slender to medium (as opposed to thick), with smooth, straight bark. The bark of young trees is between Buffy Brown (Plate XL-17-I in Ridgeway) and Olive Brown (Plate XL-17-M). Mature tree bark is Buffy Brown (Plate XL-17-I). New wood is glossy, but otherwise the bark is characteristically dull. Tree lenticals are numerous, large, and elongated. The straight branchlets tend to be slender, long- to medium-jointed, reddish-brown, and glossy. The pubescent epidermis has prominent lenticels. The branching angle of the branchlets is wide, and internodes are of medium length.

Leaves: Buds are medium in size and length, acute obtuse, and appressed. Leaf scars are prominent. The ovate leaves are approximately 3 to 3¾ inches in length, approximately 1¾ to 1¾ inches wide, and have an acute apex. The leaves are of medium thickness, and rugose. Leaf colors are as follows: top of leaf is Cedar Green (Plate VI-31-M in Ridgeway); bottom of leaf is Lettuce Green (Plate VI-31-K); midrib and stem are Pale Viridine (Plate VI-31-F). The leaf margin is finely serrated. The petiole is approximately 1 to 1½ inches in length and of medium thickness.

Figure 2:
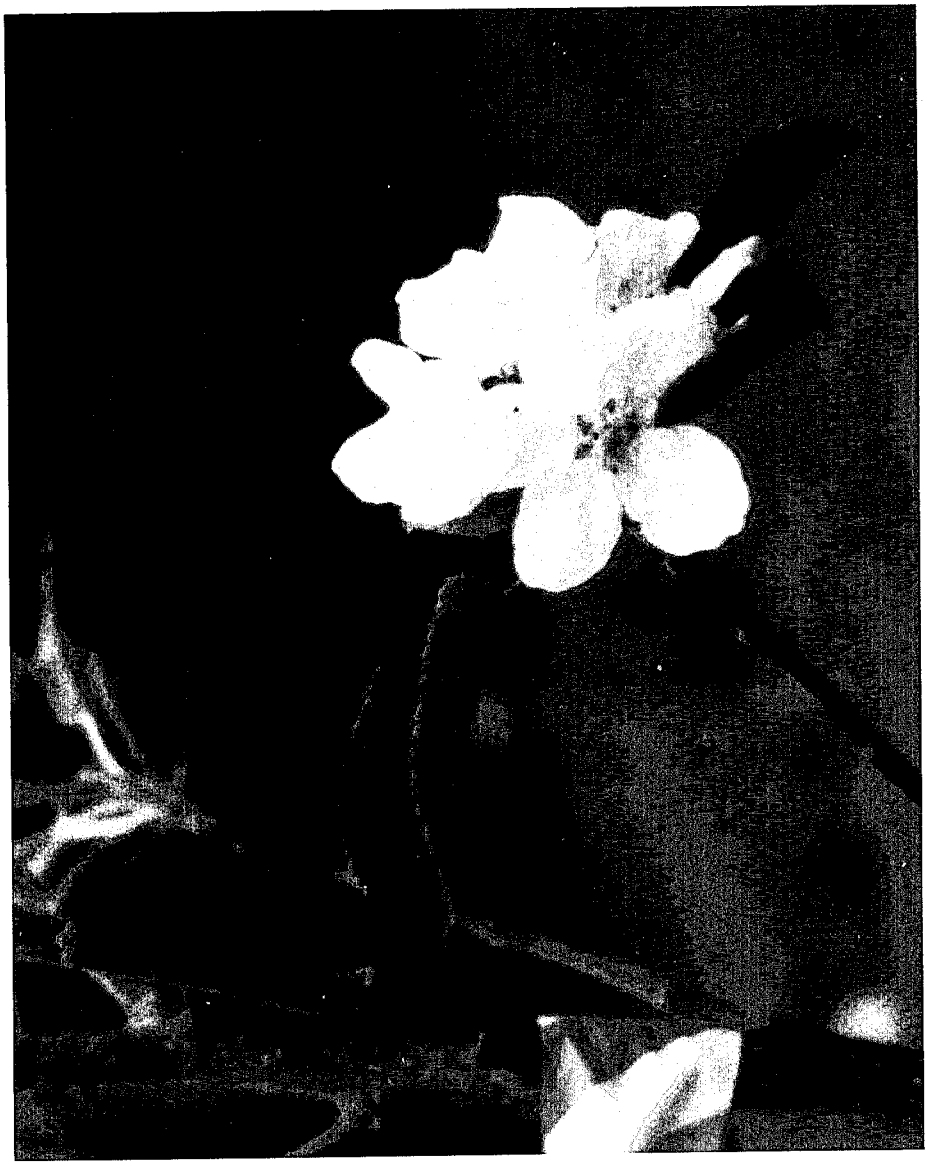
FIG. 2 is a close-up view of the blossoms in various stages of opening which depicts: petal coloration, shape, and reproductive organs of flowers; top, bottom and margin characteristics of immature leaves in varying stages of development; and the color, texture, and lenticels of bark on twigs of the claimed tree.

Flowers: As noted above, this new variety has distinctively large white blossoms (approximately 1½ to 2 inches in diameter) with open petals (FIG. 2). The flowers are partially self-fertile. The distribution of blossoms on the tree is similar to that of Red Delicious apple trees, with many flower clusters. However, the date of bloom is typically one to two days earlier than that of Red Delicious apple trees. Specifically, the bloom date of "Dulcet" in the Wenatchee, Wash. area is April 26 in an average year. This compares to the bloom date of April 28 for Red Delicious in the same area in an average year.

This new variety is a hardy, productive, and regular bearer. Its susceptibilities to insects and diseases are similar to Red Delicious apple trees.

FRUIT

The apples hang well and typically ripen 123 to 130 days from full bloom. In comparison, the maturity for Red Delicious is considered to be 145 days past full bloom.

Figure 1:
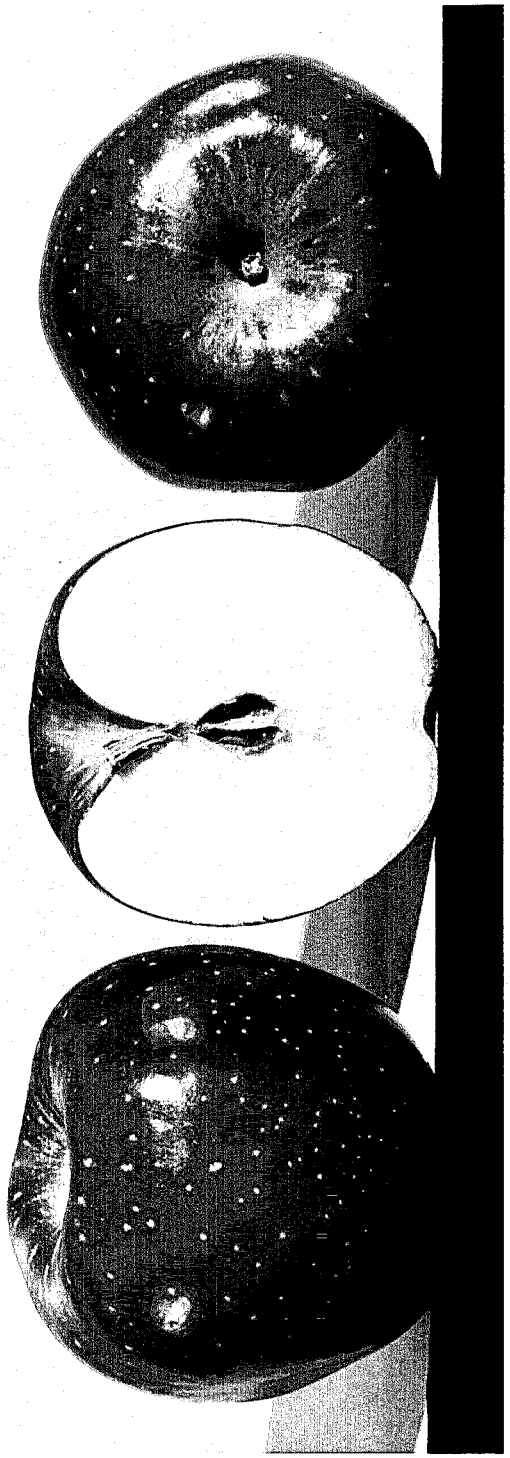
FIG. 1 (from left to right) shows: an apple in side view to depict the typical shape, color, and skin characteristics of the fruit; an apple sliced in substantially longitudinal section to show the core lines, seed cells, flesh color, and stem and stem cavity characteristics; and a view of the fruit from the stem end to depict stem cavity russet, stem length, lenticels, and shape of fruit.

Shape: The symmetrical apples are of uniform size, typically about 2¾ to 3 inches in length, about 2¾ inches in width, and have a characteristically roundish shape (FIG. 1). The stem cavity is russeted (rather than smooth), acute, and of medium width (about 1⅛ to 1¼ inch) but deep (about 9/16 to ⅝ inch). The basin is of medium depth (about ¼ to ⅜ inch) and width (about ¾ to 1 inch), obtuse, corrugated, and nonsymmetrical. The calyx end of the fruit in approximately 90% of the apples is closed. Protrusion at the calyx end of the fruit can be seen approximately 40 days from bloom. The protrusion then disappears to a roundish-shaped calyx, similar to that of a Rome apple.

Stem: As noted above, the stem is distinctively short and thick (FIG. 1).

Skin: The apple skin is of medium thickness, tough, and glossy but not waxy.

Skin color: As noted above, the apple is distinguished by a deep red ground color with large buff colored dots (FIG. 1). The conspicuous lenticel dots are numerous, round, and vary in size. The color of the skin within the stem cavity is distinctively buff to green.

Flesh: The flesh is cream white, firm, crisp, and of very good quality. The juicy, aromatic flesh has a distinctive slightly sweet, subacid taste. Pressure at harvest time, approximately 125 days from full bloom, was 15 pounds. Soluble solids were 12 Brix's, and malic acid was 0.315%. Bruising at harvest time is similar to Red Delicious.

Core: The core is median and abaxial (with the horizontal axis wider).

Figure 4B:
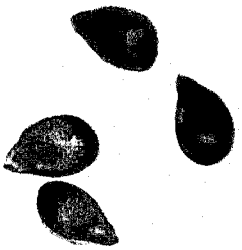
FIGS. 4A, 4B, and 4C show seeds of "Dulcet", "Red Delicious", and "Rome" varieties, respectively.
Figure 4C:
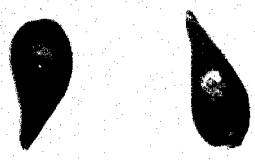
Figure 4A:
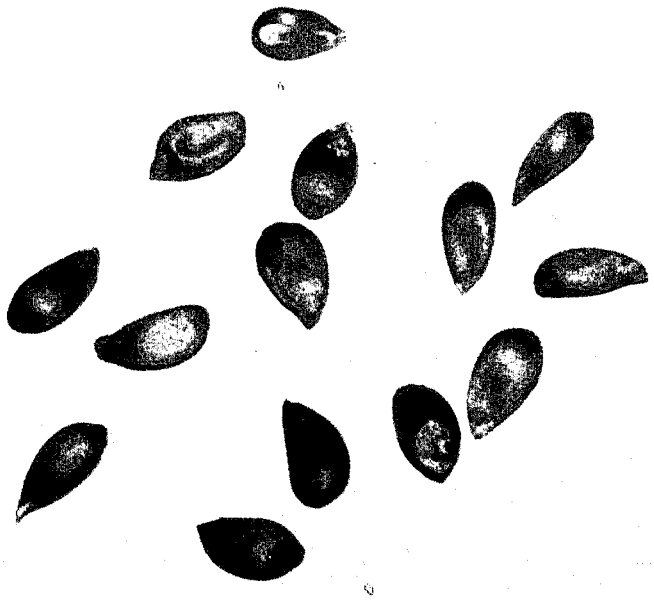

Seeds: Each apple has 2 to 3 seeds per cell and an average of 10 to 14 seeds total. At maturity, the plump seeds taper to a blunt point. FIG. 4A shows representative seeds of this new variety, as compared with seeds of Red Delicious and Rome varieties (FIGS. 4B and 4C, respectively).

Use: The fruit is a commercially marketable dessert apple of good keeping and shipping quality. Fruit storage is approximately 3 months after harvest when held in commercial storage at 30° F.

The cooking quality of the apple is good, and the flesh quality is firm after cooking.

I claim:

1. A new and distinct variety of apple tree substantially as shown and described.

* * * * *

UNITED STATES PATENT AND TRADEMARK OFFICE

CERTIFICATE OF CORRECTION

PATENT NO. : Plant 8,187

DATED : March 30, 1993

INVENTOR(S) : L. J. Bailey

It is certified that error appears in the above-identified patent and that said Letters Patent is hereby corrected as shown below:

| COLUMN | LINE | |
|---|---|---|
| 1 | 24 | "bor-deaux" should read --Bordeaux-- |
| 2 | 35 | "lenticals" should read --lenticels-- |
| 2 | 45 | "1¾ to 1¾" should read --1½ to 1¾-- |

Signed and Sealed this

Twenty-first Day of December, 1993

*Attest:*

Bruce Lehman

BRUCE LEHMAN

*Attesting Officer*

*Commissioner of Patents and Trademarks*